US010932687B2

(12) United States Patent
Thakur et al.

(10) Patent No.: US 10,932,687 B2
(45) Date of Patent: Mar. 2, 2021

(54) HARNESSING S1 VARIABILITY FOR AF DETECTION

(71) Applicant: Cardiac Pacemakers, Inc., St. Paul, MN (US)

(72) Inventors: Pramodsingh Hirasingh Thakur, Woodbury, MN (US); Qi An, Blaine, MN (US); Bin Mi, Arden Hills, MN (US); Keith R. Maile, New Brighton, MN (US); Howard D. Simms, Jr., Shoreview, MN (US); John D. Hatlestad, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 104 days.

(21) Appl. No.: 16/233,718

(22) Filed: Dec. 27, 2018

(65) Prior Publication Data

US 2019/0142290 A1 May 16, 2019

Related U.S. Application Data

(63) Continuation of application No. 15/407,991, filed on Jan. 17, 2017, now Pat. No. 10,194,819.

(Continued)

(51) Int. Cl.
*A61B 5/046* (2006.01)
*A61B 7/00* (2006.01)
(Continued)

(52) U.S. Cl.
CPC .............. *A61B 5/046* (2013.01); *A61B 5/024* (2013.01); *A61B 5/0456* (2013.01);
(Continued)

(58) Field of Classification Search
CPC ......... A61B 7/04; A61B 5/0205; A61B 5/024; A61B 7/00; A61B 5/046
(Continued)

(56) References Cited

U.S. PATENT DOCUMENTS

| 7,736,319 B2 | 6/2010 | Patangay et al. |
| 8,133,187 B2 | 3/2012 | Holmstrom et al. |

(Continued)

FOREIGN PATENT DOCUMENTS

| CN | 104244809 A | 12/2014 |
| CN | 108882913 A | 11/2018 |

(Continued)

OTHER PUBLICATIONS

"U.S. Appl. No. 15/407,991, Non Final Office Action dated Apr. 19, 2018", 11 pgs.

(Continued)

*Primary Examiner* — Amanda K Hulbert
*Assistant Examiner* — Philip C Edwards
(74) *Attorney, Agent, or Firm* — Schwegman Lundberg & Woessner, P.A.

(57) ABSTRACT

This document discusses, among other things, systems and methods to determine amplitude and morphology variations of a first heart sound over a first number of cardiac cycles, and to calculate an atrial fibrillation metric indicative of an atrial fibrillation episode of the heart using the determined amplitude and morphology variations. The systems and methods can determine a variability score using the determined amplitude and morphology variations, and can calculate the atrial fibrillation metric using the variability score.

20 Claims, 6 Drawing Sheets

Related U.S. Application Data

(60) Provisional application No. 62/281,940, filed on Jan. 22, 2016.

(51) Int. Cl.
*A61B 5/0452* (2006.01)
*A61B 5/0456* (2006.01)
*A61B 5/024* (2006.01)
*A61B 7/04* (2006.01)
*A61B 5/0402* (2006.01)

(52) U.S. Cl.
CPC ............ *A61B 5/04525* (2013.01); *A61B 7/00* (2013.01); *A61B 5/02405* (2013.01); *A61B 5/0402* (2013.01); *A61B 7/04* (2013.01); *A61B 2562/0204* (2013.01)

(58) Field of Classification Search
USPC ........................................................ 600/528
See application file for complete search history.

(56) References Cited

U.S. PATENT DOCUMENTS

| | | | |
|---|---|---|---|
| 8,155,734 B2 | 4/2012 | Li et al. | |
| 8,996,101 B2 | 3/2015 | Zhang et al. | |
| 10,194,819 B2 | 2/2019 | Thakur et al. | |
| 2008/0177191 A1* | 7/2008 | Patangay | A61B 7/04 600/509 |
| 2013/0237873 A1 | 9/2013 | Zhang et al. | |
| 2015/0342466 A1 | 12/2015 | Thakur et al. | |
| 2015/0342487 A1 | 12/2015 | Thakur et al. | |
| 2015/0342492 A1 | 12/2015 | Thakur et al. | |
| 2017/0209061 A1 | 7/2017 | Thakur et al. | |

FOREIGN PATENT DOCUMENTS

| | | |
|---|---|---|
| WO | WO-2015187365 A1 | 12/2015 |
| WO | WO-2017127355 A1 | 7/2017 |

OTHER PUBLICATIONS

"U.S. Appl. No. 15/407,991, Notice of Allowance dated Sep. 26, 2018", 6 pgs.

"U.S. Appl. No. 15/407,991, Response filed Jul. 19, 2018 to Non Final Office Action dated Apr. 19, 2018", 9 pgs.

"International Application Serial No. PCT/US2017/013762, International Search Report dated May 24, 2017", 6 pgs.

"International Application Serial No. PCT/US2017/013762, Written Opinion dated May 24, 2017", 8 pgs.

Go, Alan, et al., "Prevalence of Diagnosed Atrial Fibrillation in Adults: National Implications for Rhythm Management and Stroke Prevention: the AnTicoagulation and Risk Factors In Atrial Fibrillation (ATRIA) Study", JAMA, 285(18), (2001), 2370-2375.

Heeringa. J., et al., "Prevalence, incidence and lifetime risk of atrial fibrillation: the Rotterdam study", Eur Heart Journal (8), (2006), 949-953.

Hindricks, G., et al., "Atrial Fibrillation Detection by a Subcutaneous Monitoring Device", Computers in Cardiology 2008;35, (2008), 413-416.

Kannel, WB, et al., "Final Draft Status of the Epidemiology of Atrial Fibrillation"; Med Clin North Am. Jan. 2008 ; 92(1), (Jan. 2008), 1-25.

Purerfellner, Helmut, et al., "P-wave evidence as a method for improving algorithm to detect atrial fibrillation ininsertable cardiac monitors", Heart Rhythm Society;, (2014), 1575-1583.

"U.S. Appl. No. 15/407,991, Response filed Sep. 23, 2018 Supplement Amendment to Non Final Office Action dated Jul. 19, 2018", 9 pgs.

"Chinese Application Serial No. 201780018844.0, Office Action dated Jul. 3, 2020", w/ English Translation, 17 pgs.

"European Application Serial No. 17703271.1, Communication Pursuant to Article 94(3) EPC dated Jul. 3, 2020", 3 pgs.

"European Application Serial No. 17703271.1, Response filed Mar. 21, 2019 to Communication Pursuant to Rules 161 and 162 dated Sep. 21, 2018", 43 pgs.

"International Application Serial No. PCT/US2017/013762, International Preliminary Report on Patentability dated Aug. 2, 2018", 10 pgs.

\* cited by examiner

HARNESSING S1 VARIABILITY FOR AF DETECTION

CLAIM OF PRIORITY

This application is a continuation of U.S. application Ser. No. 15/407,991, filed Jan. 17, 2017, which claims the benefit of priority under 35 U.S.C. § 119(e) of U.S. Provisional Patent Application Ser. No. 62/281,940, filed on Jan. 22, 2016, which is herein incorporated by reference in its entirety.

BACKGROUND

Atrial fibrillation (AF) is an abnormal heart rhythm characterized by rapid and irregular beating. Atrial fibrillation is the most common serious abnormal heart rhythm, with over 5 million diagnoses in Europe and North America alone. As the prevalence of atrial fibrillation rises with age, incidence of atrial fibrillation is expected to raise with the aging population.

TECHNICAL FIELD

This document relates generally to detection of atrial fibrillation and particularly, but not by way of limitation, to harnessing heart sound variability for atrial fibrillation detection.

OVERVIEW

This document discusses, among other things, systems and methods to determine amplitude and morphology variations of a first heart sound over a first number of cardiac cycles, and to calculate an atrial fibrillation metric indicative of an atrial fibrillation episode of the heart using the determined amplitude and morphology variations. The systems and methods can determine a variability score using the determined amplitude and morphology variations, and can calculate the atrial fibrillation metric using the variability score.

This overview is intended to provide an overview of subject matter of the present patent application. It is not intended to provide an exclusive or exhaustive explanation of the disclosure. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Atrial fibrillation (AF) can be detected in a number of ways, such as using an implantable device with an atrial lead, a 12-lead electrocardiogram (ECG), etc. Insertable Cardiac Monitors (ICM), or other implantable devices with or without an atrial lead (e.g., single-chamber Implantable Cardioverter Defibrillators (ICD), subcutaneous ICDs, extravascular ICDs, etc.) or wearable or external sensors largely employ R-R variability based algorithms for atrial fibrillation detection. However, many ICM and wearable algorithms using R-R variability based algorithms show poor real-world performance, and require long windows of data collection (e.g., 2 or more minutes, etc.) to overcome noisy R detections and to keep performance of the detection reasonably accurate.

Figure 1:
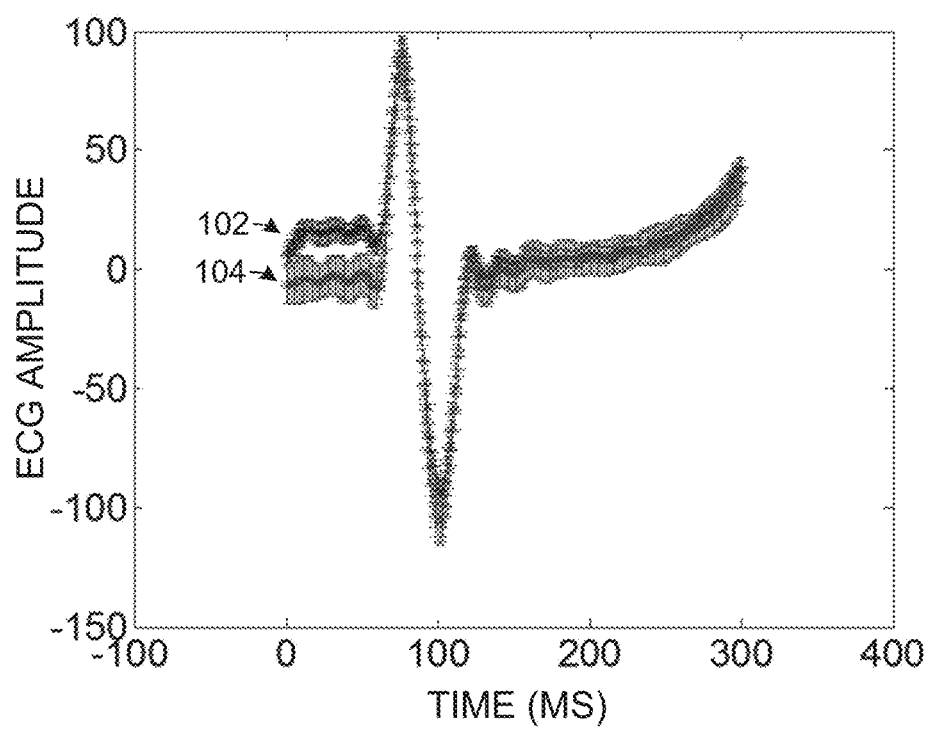
FIG. 1 illustrates generally example electrocardiogram (ECG) signals including a first ECG signal of a heart in normal sinus rhythm over a first set of cardiac intervals and an ECG signal of a heart in atrial fibrillation over a second set of cardiac intervals.

FIG. 1 illustrates generally example electrocardiogram (ECG) signals including a first ECG signal 102 of a heart in normal sinus rhythm over a first set of cardiac intervals and an ECG signal 104 of a heart in atrial fibrillation over a second set of cardiac intervals.

To assist atrial fibrillation detection, R-R variability based detection algorithms can be augmented with other ECG-related detection criteria, such as P-wave detection. In P-wave detection, a pre-R window can be averaged for consecutive beats that meet an R rate and variability criteria, P-wave features (e.g., flutter, noise, etc.) can be identified, or P-wave evidence can be accumulated over a detection window.

The present inventors have recognized, among other things, that atrial fibrillation can be detected using heart sounds (HS). Heart sounds are recurring mechanical signals associated with cardiac vibrations from and blood flow through the heart with each cardiac cycle, and can be separated and classified according to activity associated with the vibrations and blood flow. The first heart sound (S1) is the vibrational sound made by the heart during closure of the atrioventricular (AV) valves. The second heart sound (S2) is the beginning of diastole, and is made by the aortic and pulmonary valves. The third and fourth heart sounds (S3, S4) are related to filling pressures of the left ventricle during diastole.

S1 amplitude can be variable during atrial fibrillation, reflecting variable beat-to-beat filling of the heart during an atrial fibrillation episode. A short R-R interval can be indicative of less filling, lower contractility, and a muffled S1 (e.g., lower amplitude) in a subsequent cardiac cycle. A long R-R interval can be indicative of more filling, a higher contractility, and a loud S1 (e.g., higher amplitude) in a subsequent cardiac cycle.

The present inventors have recognized that, in addition to S1 amplitude variability, the morphology variability of the S1 heart sound can be used, separate from or in addition to S1 amplitude variability, to detect atrial fibrillation. Whereas R-R variability based atrial fibrillation detection can require a long period (e.g., 2 minutes or greater), many atrial fibrillation episodes can occur during shorter periods. The present inventors have recognized, among other things, that amplitude and morphology variability of the S1 heart sound can be used to detect atrial fibrillation in a shorter time period, and thus, more atrial fibrillation episodes (e.g., shorter atrial fibrillation episodes), and, in certain examples, with greater accuracy, than using R-R variability based atrial fibrillation detection. Further, R-R variability can change with other physiologic variables, such as contractility, exercise tolerance, cardiac output, etc. Accordingly, amplitude and morphology variability, in certain examples, can provide a more robust atrial fibrillation detection algorithm.

Figure 2A:
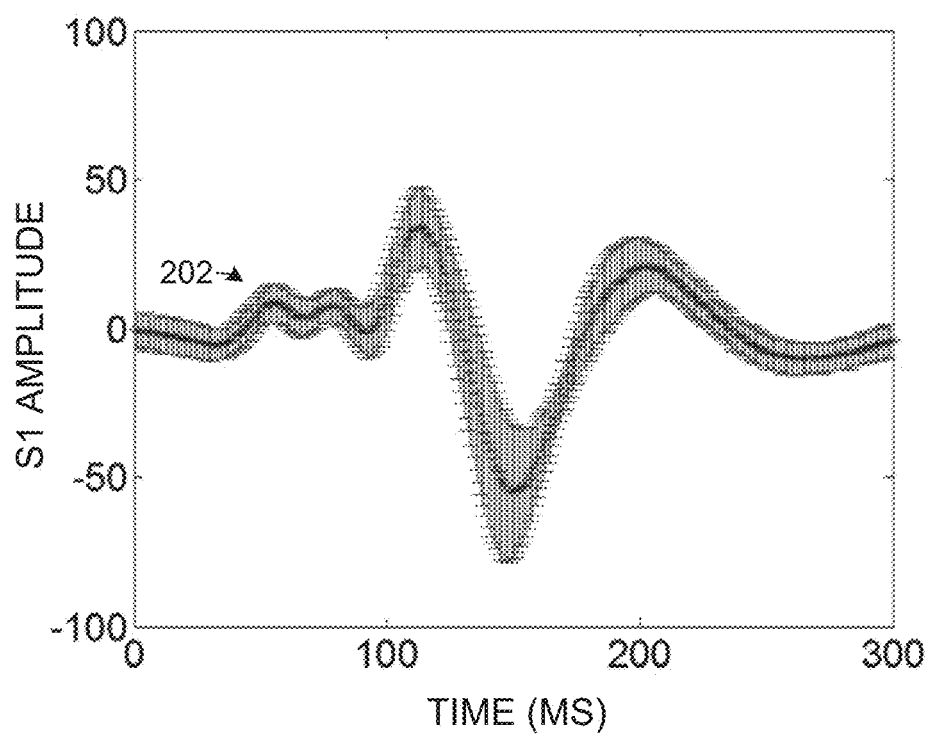
FIGS. 2A-B illustrate generally example heart sound signals including a first S1 heart sound signal of a heart in normal sinus rhythm over a first set of cardiac and a second S heart sound signal of a heart in atrial fibrillation over a second set of cardiac intervals.
Figure 2B:
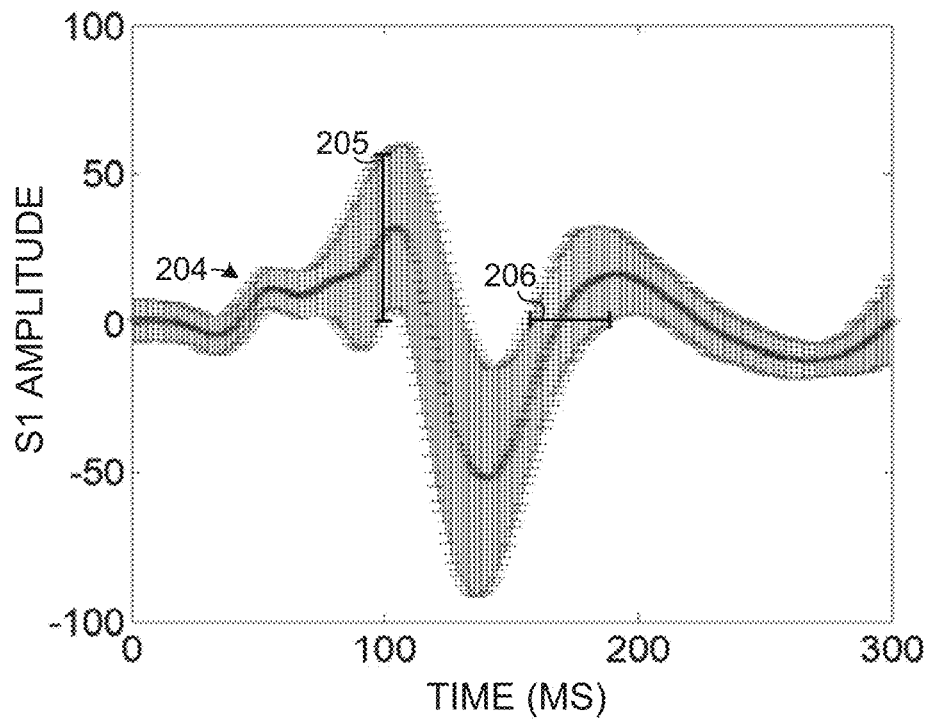

FIGS. 2A-B illustrate generally example heart sound signals including a first S1 heart sound signal 202 of a heart in normal sinus rhythm over a first set of cardiac intervals (e.g., 50 cardiac intervals) and a second S1 heart sound signal 204 of a heart in atrial fibrillation over a second set of cardiac intervals (e.g., 50 cardiac intervals).

Whereas R waves of an ECG signal align in sinus rhythm and in atrial fibrillation, as illustrated in FIG. 1, the S1 heart sound illustrates greater vertical (e.g., amplitude) variability 205 and horizontal (morphology) variability 206 in atrial fibrillation than in normal sinus rhythm, as illustrated in FIGS. 2A-B. Horizontal variability 206 in the S1 heart sound can be indicative of beat-to-beat variability in R-S1 timing or S1 morphology variability.

Figure 3:
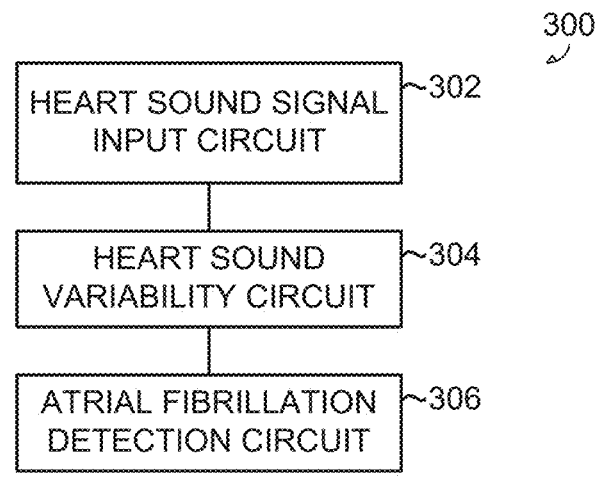
FIG. 3 illustrates generally an example system including a heart sound (HS) signal input circuit, a heart sound variability circuit, and an atrial fibrillation detection circuit.

FIG. 3 illustrates generally an example system 300 including a heart sound (HS) signal input circuit 302, a heart sound variability circuit 304, and an atrial fibrillation detection circuit 306. The heart sound signal input circuit 302 can be configured to receive heart sound information of a heart over a first interval. In an example, the heart sound information can include a heart sound signal, a portion of a heart sound signal, or information about a heart sound signal or a portion of a heart sound signal from one or more other devices, such as a heart sound detector. In certain examples, the heart sound information can include at least a portion of the heart sound signal, and the variability circuit 304 can be configured to detect a first heart sound in the heart sound signal.

The first interval can include at least a portion of each of a first number of cardiac cycles. For example, the first interval can include a number of cardiac cycles (e.g., 1, 3, 5, 10, 50, etc.), a number of cardiac cycles over a time interval (e.g., 5 seconds, 10 seconds, 30 seconds, 1 minute, etc.), a portion of a number of cardiac cycles (e.g., a specific heart sound window (such as an S1 window, or the time over which an S1 heart sound occurs or is expected to occur) over a number of cardiac cycles), or a portion of a number of cardiac cycles over a time interval. In certain examples, the first interval can include a minimum number of cardiac cycles (e.g., greater than 1) within a specified time interval (e.g., 60 cardiac cycles within 1 minute, 10 cardiac cycles within 10 seconds, 10 cardiac cycles within 7 seconds, etc.).

The heart sound variability circuit 304 can be configured to receive heart sound information (e.g., a heart sound signal) from the heart sound signal input circuit 302, and to determine an amplitude variation or a morphology variation of at least a portion of a first heart sound over the first interval (e.g., a number of cardiac cycles). Amplitude variation can include, generally, a vertical variation of the first heart sound at one or more fiducial points over the first interval. Morphology variation can include, generally, one or more of a horizontal variation of the first heart sound at one or more of the same or other fiducial points over the first interval, a variation of a shape of the first heart sound at one or more points over the first interval, or a shift in time of one or more fiducial points or features of the first heart sound with respect to one or more other points or features.

Amplitude variation can include, for example, a difference in magnitude of a first heart sound (S1) of the heart sound information over the first interval (e.g., a number of cardiac cycles) at a specific time of the first heart sound, such as illustrated as a vertical variability 205 in FIG. 2B. In other examples, the amplitude variation can include the difference in magnitude of the first heart sound at one or more other times of or along the first heart sound. The amplitude variation can include the difference in magnitude at a fiducial point, or a sum of magnitudes at one or more fiducial points, or between different points (e.g., integration of a difference in magnitude along a string of points or a portion of the heart sound, etc.). In certain examples, the amplitude variation can include a difference in magnitude of a feature of the first heart sound over the first interval, such as one or more peaks or troughs of the first heart sound over the first interval, or between one or more peaks, troughs, or between a peak and a trough, or two or more other points of the first heart sound over the first interval.

Morphology variation can include, for example, a variation in a shape of a first heart sound (S1) (e.g., at least a portion of the first heart sound) of the heart sound information over the first interval (e.g., a number of cardiac cycles). In an example, the variation in the shape of the first heart sound can include a time variation of at least a portion of the first heart sound over the first interval, such as illustrated as horizontal variability 206 in FIG. 2B. In other examples, the morphology variation can include a time shift between features of the first heart sound (e.g., between an S1 peak and trough, between zero crossings, between the S1 peak and one or more subsequent zero crossings, etc.), or between one or more features of the first heart sound and another physiologic feature (e.g., between an S1 component, such as the S1 peak, and another heart sound feature, such as an S2 peak or one or more other heart sound feature; a feature of an ECG signal, such as a portion of an R wave or one or more other feature of an ECG signal; one or more other physiologic feature; etc.). In an example, the morphology variation can include a latency of one or more features of the first heart sound with respect to the R wave of the ECG signal, or a variance in latency of the one or more feature with respect to the R wave of the ECG signal over the first interval.

In an example, the variation in shape of the first heart sound can include a variation in an offset between first and second features of the first heart sound in a first cardiac cycle and an offset between the first and second features of the first heart sound in a second cardiac cycle. The first and second cardiac cycles can be cardiac cycles in the first interval. In another example, the variation in shape of the first heart sound can include a variation in an offset between a first feature over the first interval and a second feature over the first interval.

In other examples, the variation in shape of the first heart sound can include a variation in a function of a first-order derivative (e.g., a slope), or a higher-order derivative, of a portion of the first heart sound over the first interval, or a variation in a function of a first- or higher-order derivative of the portion of the first heart sound in a first cardiac cycle and a function of a first- or higher-order derivative of the portion of the first heart sound in a second cardiac cycle.

In an example, the variation in shape can include an aggregate difference in shape between at least a portion of the first heart sound over the first interval, or between at least a portion of the first heart sound of at least one cardiac cycle and a template (e.g., a patient-specific heart sound template, a general heart sound template, etc.). In other examples, one or more other morphology operations, or differences in a shape or time of at least a portion of the first heart sound, can be used.

The atrial fibrillation detection circuit 306 can be coupled to the heart sound variability circuit 304, and can be configured to calculate an atrial fibrillation metric indicative of an atrial fibrillation episode of the heart for the first interval using the determined amplitude and morphology variations. In certain examples, the atrial fibrillation detection circuit 306 can calculate the atrial fibrillation metric using either the amplitude variation or the morphology variation (e.g., a timing, a first- or higher-order derivative, or other shape difference, etc.), absent the other, or using a combination of amplitude or morphology variations (e.g., including multiple morphology variations, etc.).

In an example, the atrial fibrillation detection circuit 306, or one or more other circuits or components, can be configured to provide information or an alert, such as to a user, a clinician, or to one or more circuits or systems, using one or more of the amplitude variation, the morphology variation, the variability score, or the atrial fibrillation metric. In other examples, the atrial fibrillation detection circuit 306, or one or more other circuits or components, one or more of the amplitude variation, the morphology variation, the variability score, or the atrial fibrillation metric can be used to provide or alter a treatment or therapy, such as antitachycardia pacing (ATP) (e.g., burst pacing), vagus nerve stimulation, drug delivery, or one or more other therapies, for example, to alter or alleviate a detected atrial fibrillation.

Figure 4:
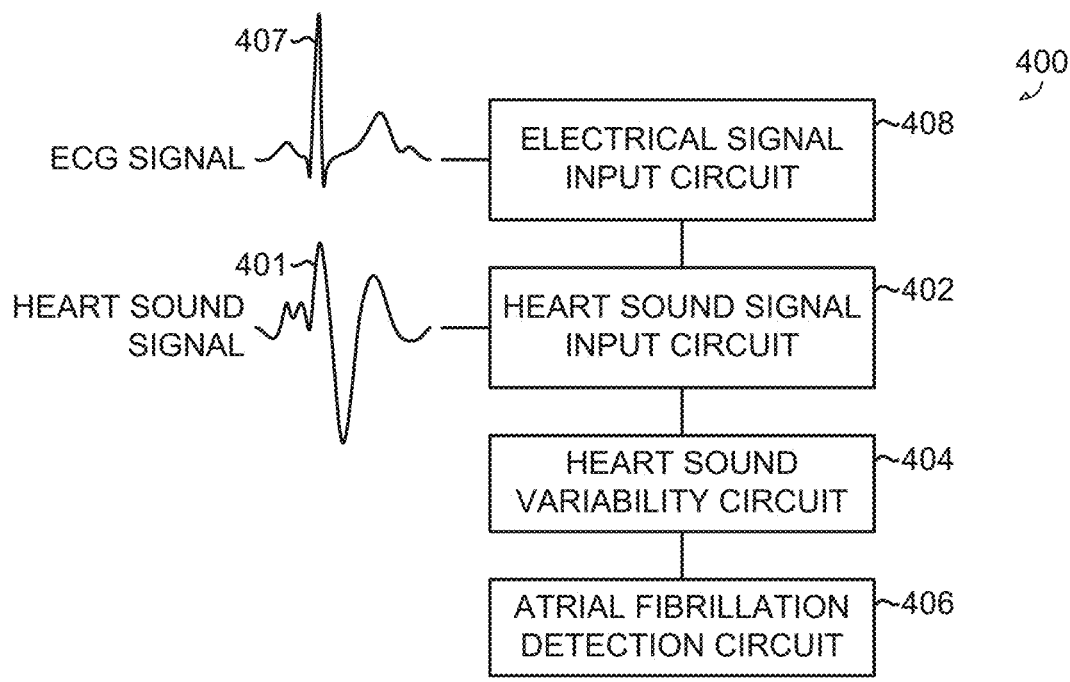
FIG. 4 illustrates generally an example system including an electrical signal input circuit, a heart sound signal input circuit, a heart sound variability circuit, and an atrial fibrillation detection circuit.

FIG. 4 illustrates generally an example system 400 including an electrical signal input circuit 408, a heart sound signal input circuit 402, a heart sound variability circuit 404, and an atrial fibrillation detection circuit 406.

The electrical signal input circuit 408 can be configured to receive an electrical signal of the heart, such as an ECG signal 407, or information about the electrical signal, such as a time of an R wave of the electrical signal, etc., over a first interval and to provide information from or about the electrical signal of the heart (e.g., a time of the R wave, etc.) to the heart sound signal input circuit 402.

The heart sound signal input circuit 402 can be configured to receive heart sound information of the heart, such as at least a portion of a heart sound signal 401, over the first interval, and to detect the first heart sound (e.g., S1) using the electrical signal of the heart. In an example, the heart sound signal input circuit 402 can establish an S1 window using the electrical signal of the heart, or information about the electrical signal of the heart.

The heart sound variability circuit 404 can be configured to determine an amplitude and morphology variation of the first heart sound over the first interval, such as described herein, and the atrial fibrillation detection circuit 406 can be configured to calculate an atrial fibrillation metric indicative of an atrial fibrillation episode of the heart for the first interval using the determined amplitude and morphology variations.

In an example, the heart sound variability circuit 404 can be configured to determine a variability score of the first heart sound for the first interval using at least one of the determined amplitude and morphology variations. Various approaches can be used. For example, the heart sound variability circuit 404 can be configured to decompose at least a portion of the first heat sound into amplitude variability and shape variability metrics, and can use the amplitude variability and shape variability metrics in predefined or patient-specific proportions based on the quality or efficacy of each metric in a given patient or across a specified population. For example, in patients having more amplitude variability during non-AF periods than shape variability, less weight can be afforded to the amplitude variability metric.

In an example, the heart sound variability circuit 404 can decompose at least a portion of the first heart sound into amplitude variability and shape variability metrics using at least one of a linear algebra or vector analysis based approach, a simple fiducial point based approach, a template or baseline based approach, or one or more other approaches. The variability score can include, among other things, a number or other mathematical expression (e.g., a vector, etc.) indicating a magnitude of the variance in relation to a baseline or other template for either the patient or a population.

In an example, the atrial fibrillation detection circuit 406 can be configured to calculate the atrial fibrillation metric using, among other things, the variability score. In certain examples, the variability score can be one factor of a larger algorithm that considers one or more other physiologic variables. In certain examples, the variability score can be used to alter a weighting of one or more physiologic variables used to calculate the atrial fibrillation metric, including the weighting of one or more amplitude or morphology variations described herein.

In certain examples, the atrial fibrillation detection circuit 406, or one or more other circuits or components, can be configured to provide information or an alert, or to provide or alter a treatment or therapy, such as described above.

Figure 5:
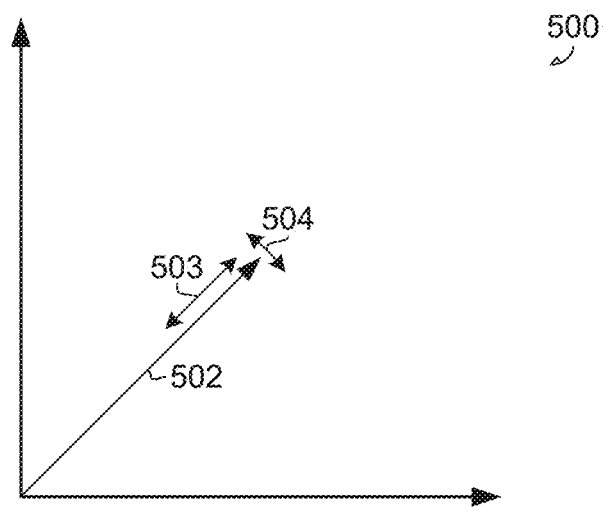
FIG. 5 illustrates generally an example N-D space including a first heart sound vector having a scale that represents an amplitude variability and a direction that represents morphology variability.

FIG. 5 illustrates generally an example N-D space 500 including a first heart sound vector 502 having a scale 503 that represents an amplitude variability and a direction 504 that represents morphology variability. In an example, the morphology variability can include shape variability, a time variability, or one or more other morphology variations, as described herein. In an example, a heart sound variability circuit (e.g., 304, 406, etc.) can use a linear algebra or vector based analysis to determine one or more of the scale 503 or the direction 504 of the vector 502, for example, using equations 1 and 2, respectively, below, where x represents the heart sound information over the first interval, and y represents a template or baseline.

$$\text{scale} = \sqrt{\sum_1^N (x_i^2)} - \sqrt{\sum_1^N (y_i^2)} \quad (1)$$

$$\text{direction} = \frac{\sum_1^N (x_i - \bar{x})(y_i - \bar{y})}{\sqrt{\sum_1^N (x_i - \bar{x})^2} \sqrt{\sum_1^N (y_i - \bar{y})^2}} \quad (2)$$

Figure 6:
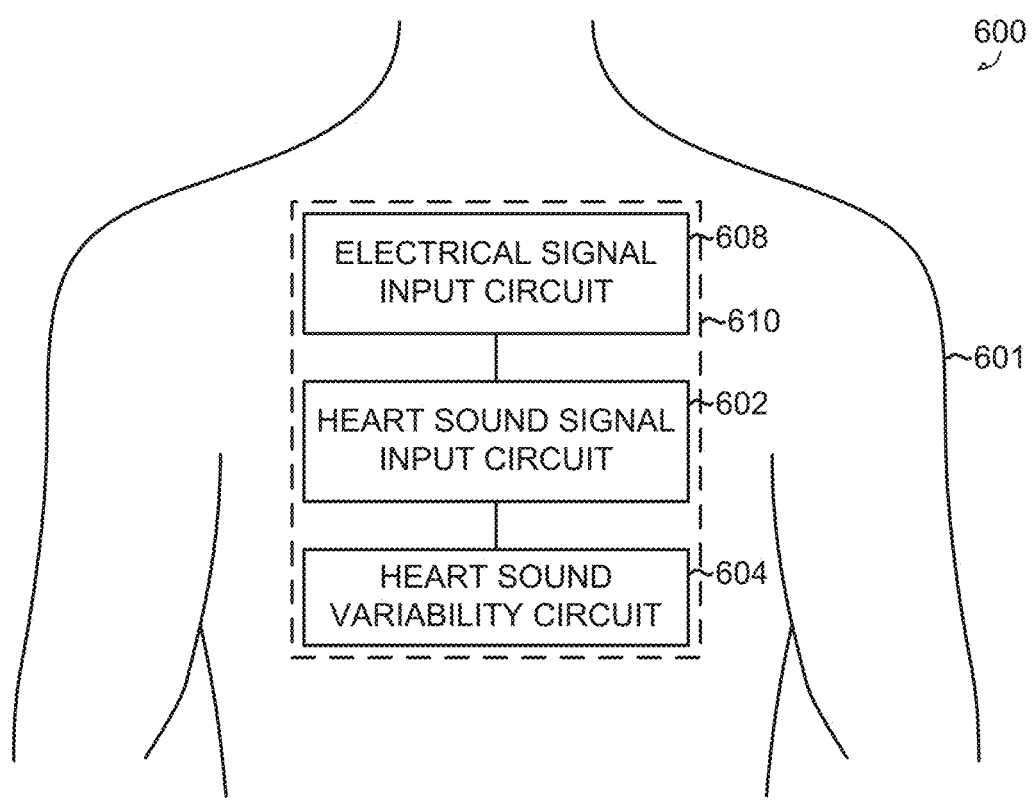
FIG. 6 illustrates generally an example system including an implantable device, such as an implantable cardiac rhythm or heart failure management device, or one or more other management or therapy devices configured to detect heart sound information of a patient.

FIG. 6 illustrates generally an example system 600 including an implantable device 610, such as an implantable cardiac rhythm or heart failure management device, or one or more other management or therapy devices configured to detect heart sound information of a patient 601. In an example, the implantable device 610 can include an electrical signal input circuit 608 configured to receive an electrical signal of a heart of the patient 601 over a first interval, a heart sound signal input circuit 602 configured to receive a heart sound signal from the patient 601 over the first interval and to detect a first heart sound (S1) of the heart sound signal, and a heart sound variability circuit 604 configured to determine an amplitude and morphology variation of the first heart sound over the first interval.

In an example, the implantable device 610 can include an atrial fibrillation detection circuit configured to calculate an atrial fibrillation metric indicative of an atrial fibrillation episode, or one or more other system components described herein. In other examples, the implantable medical device 610 can be configured to detect a heart sound signal of a heart, such as using an accelerometer or other heart sound detection device, and to transmit heart sound information outside of the implantable device 610 for processing. In certain examples, one or more of the amplitude or morphology variations, a variability score, or an atrial fibrillation metric can be determined outside of the implantable device 610.

In other examples, one or more system components, such as a heart sound detector, can be included in the implantable device 610 or one or more other devices, such as an insertable cardiac monitor (ICM) or other subcutaneous device, an injectable device, or a wearable or other external device, and one or more of the heart sound signal input circuit 602, the heart sound variability circuit 604, and the atrial fibrillation detection circuit 606 can be an external component, depending on system design and requirements.

Figure 7:
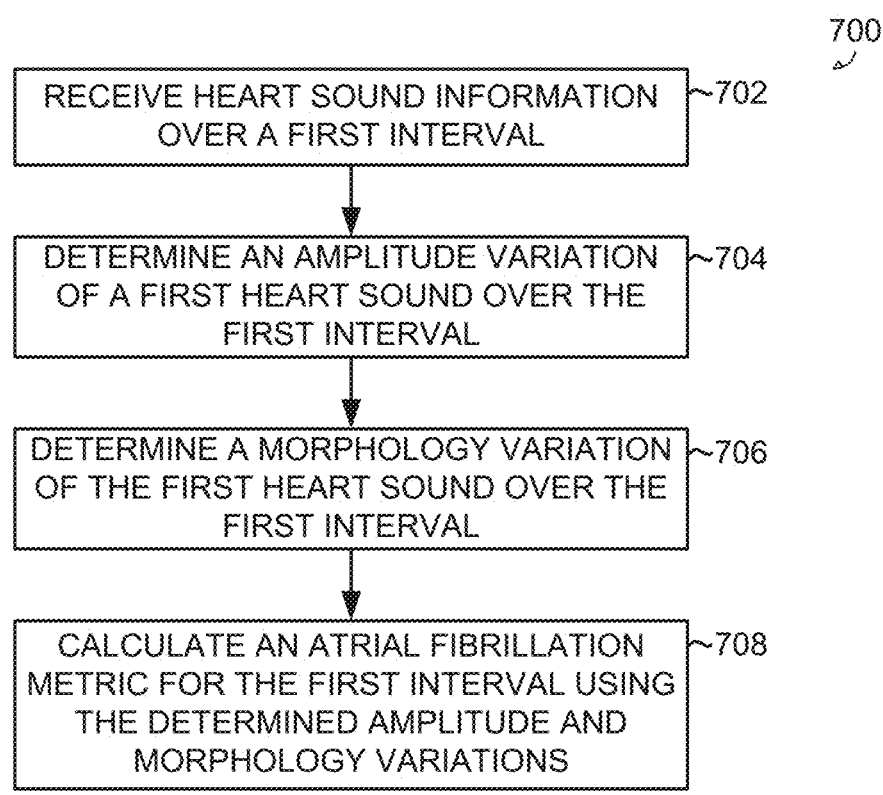
FIG. 7 illustrates generally an example method for calculating an atrial fibrillation metric using determined amplitude and morphology variations of a first heart sound.

FIG. 7 illustrates generally an example method 700 for calculating an atrial fibrillation metric using determined amplitude and morphology variations of a first heart sound.

At 702, heart sound information can be received over a first interval, such as using a heart sound signal input circuit. In an example, heart sound information can be detected using an internal or external heart sound detector (e.g., an accelerometer), and the heart sound signal input circuit can be configured to receive heart sound information from the heart sound detector. In other examples, the heart sound signal input circuit includes a heart sound detector configured to detect heart sound information of the heart over the first interval. A first heart sound (S1) can be detected, or information about the first heart sound can be detected, using the heart sound signal or heart sound information.

At 704, an amplitude variation of the first heart sound is determined over the first interval, such as using a heart sound variability circuit. At 706, a morphology variation of the first heart sound is determined over the first interval, such as using the heart sound variability circuit. In certain examples, only one of the amplitude or morphology variations are determined and used to calculate the atrial fibrillation metric. In an example, different kinds of morphology variation can be determined, such as described above, and, in certain examples, combined to form one morphology variation.

At 708, an atrial fibrillation metric indicative of an atrial fibrillation episode of the heart for the first interval can be calculated using one or more of the amplitude or morphology variations, such as using an atrial fibrillation detection circuit. In certain examples, the heart sound variability circuit can be configured to determine a variability score of the first heart sound for the first interval using both the amplitude and morphology variations, and the atrial fibrillation detection circuit can be configured to calculate the atrial fibrillation metric using the variability score.

In an example, the atrial fibrillation metric can include a metric indicative of whether or not an atrial fibrillation has occurred, such as a likelihood (e.g., from 0 to 10, etc.) computed based on a comparison of the at least one of the amplitude or morphology variations, or the variability score, to a template, a history, or a baseline. In other examples, the atrial fibrillation metric can include a count of a number of atrial fibrillation occurrences, or a count of a number of likely atrial fibrillation occurrences, for example, using the amplitude or morphology variations, or the variability score (e.g., if one or more of the variations or variability scores exceeds a threshold, etc.).

In an example, one or more of the amplitude or morphology variations or the variability score can be determined using a linear algebra or vector based analysis in an N-D space. In certain examples, beat-by-beat amplitude or morphology assessments can be made, such as using external, off-line data processing in a programmer or other external computer system, or leveraging efficient correlation implantable correlation methods. In other examples, a fiducial point based approach can be used, where fiducial points, such as a set of peaks, troughs, peak-to-peak, peak-to-trough, or other fiducial points can used as representative features to be decomposed into amplitude variability or morphology variability metrics. Features can be matched across beats and correlated to provide variability metrics, including amplitude or morphology changes, such as temporal shifts or shape changes of features with respect to other features or physiologic signals or makers.

In other examples, one or more of the amplitude or morphology variations or the variability score can be determined using a template based approach. One or more templates for a specific patient or a target population can be created either during or outside of atrial fibrillation. A beat-by-beat assessment of deviation or similarity to the amplitude or morphology of one or more templates can be determined and used to provide one or more of the amplitude or morphology variations, the variability score, or the atrial fibrillation metric. In certain examples, the template based approach can be used to determine morphology variations, while one or more other approaches (e.g., fiducial point, linear algebra, etc.) can be used to determine amplitude variations.

In an example, an activity sensor (e.g., accelerometer, etc.) can be used to determine if the patient is active or inactive, and one or more of the amplitude or morphology variations or the variability score can be applied for atrial fibrillation detection only during an inactive phase to increase sensitivity of the heart sound detection. A posture senor can be used to determine patient position. In certain examples, heart sounds can be detected, or amplitude or morphology variations can be determined, only during periods of inactivity, rest, or while the patient is in a specific position (e.g., lying down, or not during periods of posture change, etc.) or set of positions, for example, to increase accuracy or decrease false positives. In an example, step changes in variability can be removed, for example, due to activity, increased heart rate, posture, or change in posture, such as using a high-pass filter, a step change in values between intervals or cardiac cycles, or other mechanism.

In other examples, amplitude or morphology variations of one or more contractility-related portions of the first heart sound can be compared to one or more other variations of the heart sound or other physiologic variable, and removed if the variations of the contractility-related portion of the first heart sound is similar to the one or more other variations. In an example, activity or posture information can be used to determine an adaptive S1 variability threshold for atrial fibrillation detection.

In certain examples, multiple variabilities can be combined in a patient or population specific manner, such as using a logical or a linear combination of individual detections. For example, atrial fibrillation detection can be made using a logical combination of individual detections, including one or more of S1 amplitude variability, S1 morphology variability, R-R variability, or one or more other physiologic parameters, using one or more of the detection approaches described herein. Various output can be used to determine or provide an indication of variability, such as a Lorentz plot, illustrating the shape variability of a current cardiac cycle versus the shape variability of the previous cardiac cycle. In other examples, other outputs can be used.

In other examples, atrial fibrillation detection can be made using a linear combination of individual detections, such as using a weighted combination of one or more of the amplitude or morphology variabilities described herein. In certain examples, the weighted combinations can be compared to one or more thresholds. The weights of the specific variables can be dependent upon, for example, variability of each parameter during non-AF periods. Detection of atrial fibrillation can be made, for example, using a composite score of such weighted variabilities.

Figure 8:
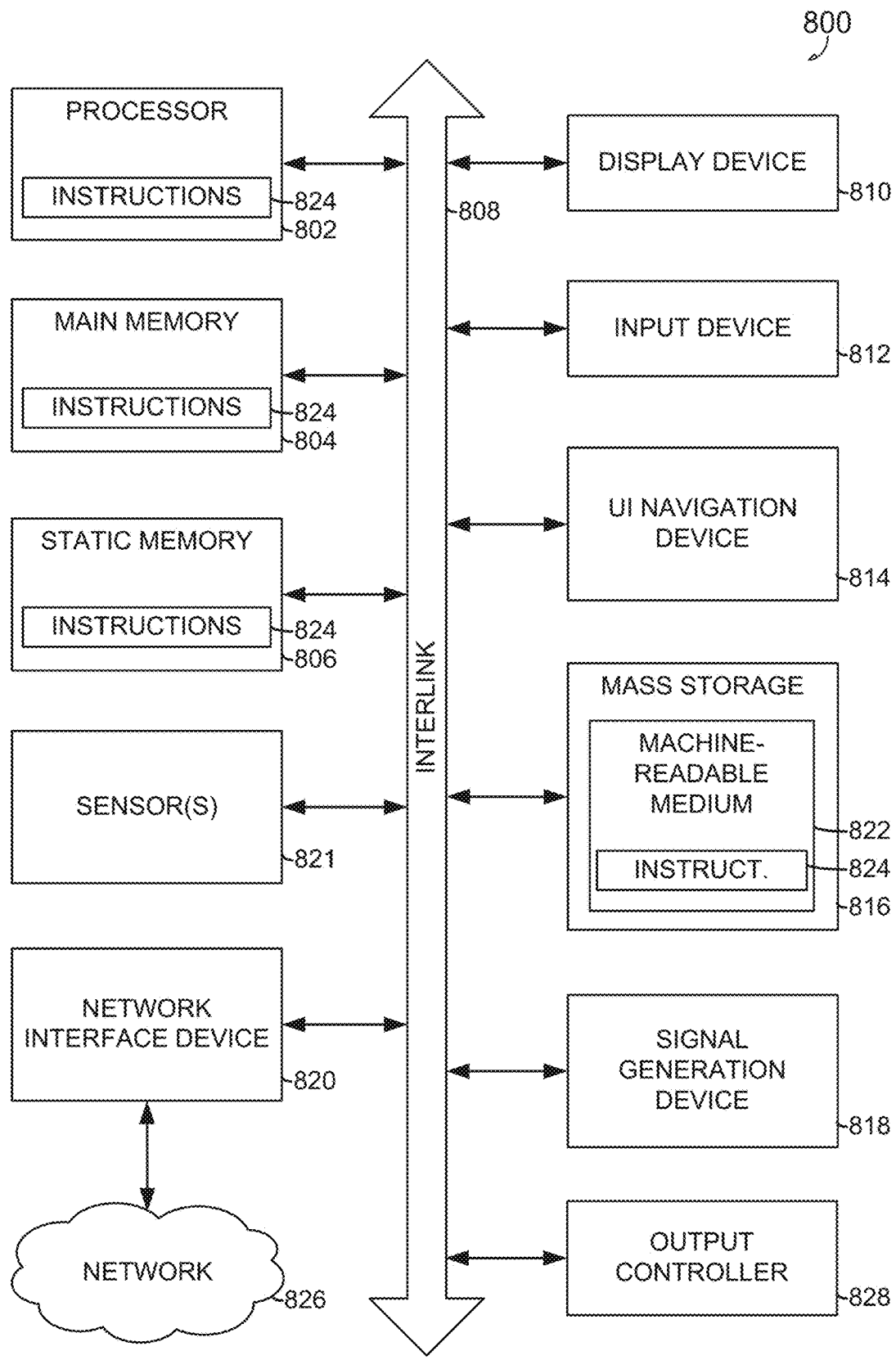
FIG. 8 illustrates generally a block diagram of an example machine upon which any one or more of the techniques (e.g., methodologies) discussed herein may perform.

FIG. 8 illustrates generally a block diagram of an example machine 800 upon which any one or more of the techniques (e.g., methodologies) discussed herein may perform. In alternative embodiments, the machine 800 may operate as a standalone device or may be connected (e.g., networked) to other machines. In a networked deployment, the machine 800 may operate in the capacity of a server machine, a client machine, or both in server-client network environments. In an example, the machine 800 may act as a peer machine in peer-to-peer (P2P) (or other distributed) network environment. The machine 800 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 800 may include a hardware processor 802 (e.g., a central processing unit (CPU), a graphics processing unit (GPU), a hardware processor core, or any combination thereof), a main memory 804 and a static memory 806, some or all of which may communicate with each other via an interlink (e.g., bus) 808. The machine 800 may further include a display unit 810 (e.g., a raster display, vector display, holographic display, etc.), an alphanumeric input device 812 (e.g., a keyboard), and a user interface (UI) navigation device 814 (e.g., a mouse). In an example, the display unit 810, input device 812 and UI navigation device 814 may be a touch screen display. The machine 800 may additionally include a storage device (e.g., drive unit) 816, a signal generation device 818 (e.g., a speaker), a network interface device 820, and one or more sensors 821, such as a global positioning system (GPS) sensor, compass, accelerometer, or other sensor. The machine 800 may include an output controller 828, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 816 may include a machine readable medium 822 on which is stored one or more sets of data structures or instructions 824 (e.g., software) embodying or utilized by any one or more of the techniques or functions described herein. The instructions 824 may also reside, completely or at least partially, within the main memory 804, within static memory 806, or within the hardware processor 802 during execution thereof by the machine 800. In an example, one or any combination of the hardware processor 802, the main memory 804, the static memory 806, or the storage device 816 may constitute machine readable media.

While the machine readable medium 822 is illustrated as a single medium, the term "machine readable medium" may include a single medium or multiple media (e.g., a centralized or distributed database, and/or associated caches and servers) configured to store the one or more instructions 824.

The term "machine readable medium" may include any medium that is capable of storing, encoding, or carrying instructions for execution by the machine 800 and that cause the machine 800 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 824 may further be transmitted or received over a communications network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 820 may include one or more physical jacks (e.g., Ethernet, coaxial, or phone jacks) or one or more antennas to connect to the communications network 826. In an example, the network interface device 820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 800, and includes digital or analog communications signals or other intangible medium to facilitate communication of such software.

Additional Notes and Examples

In Example 1, a system includes a heart sound signal input circuit configured to receive heart sound information of a heart over a first interval, the first interval including at least a portion of each of a first number of cardiac cycles, a heart sound variability circuit configured to determine an amplitude variation of a first heart sound of the heart sound information over the first interval or to determine a morphology variation of the first heart sound over the first interval, and an atrial fibrillation detection circuit configured to calculate an atrial fibrillation metric indicative of an atrial fibrillation episode of the heart for the first interval using the determined amplitude variation or morphology variation.

In an example, the heart sound variability circuit can be configured to determine the amplitude variation and the morphology variation, and the atrial fibrillation detection circuit can be configured to calculate the atrial fibrillation metric using the determined amplitude and morphology variations.

In Example 2, the heart sound variability circuit of Example 1 is optionally configured to determine a variability score of the first heart sound for the first interval using the determined amplitude and morphology variations.

In Example 3, the atrial fibrillation detection circuit of any one or more of Examples 1-2 is optionally configured to calculate the atrial fibrillation metric using the variability score.

In Example 4, any one or more of Examples 1-3 optionally includes an electrical signal input circuit configured to receive an electrical signal of the heart over the first interval, wherein the heart sound information includes a heart sound signal of the heart, and wherein the heart sound signal input circuit is configured to detect the first heart sound of the heart sound signal using the electrical signal of the heart.

In Example 5, any one or more of Examples 1-4 optionally include an implantable medical device including the heart sound signal input circuit, the electrical signal input circuit, and the heart sound variability circuit, wherein the heart sound variability circuit is coupled to the heart sound signal and electrical signal input circuits.

In Example 6, the morphology variation of the first heart sound of any one or more of Examples 1-5 optionally includes a variation in a shape of the first heart sound.

In Example 7, the variation in the shape of the first heart sound of any one or more of Examples 1-6 optionally includes a variation in an offset between first and second features of the first heart sound in a first cardiac cycle and an offset between the first and second features of the first heart sound in a second cardiac cycle.

In Example 8, the variation in the shape of the first heart sound of any one or more of Examples 1-7 optionally includes a variation in a function of a first- or higher-order derivative of a portion of the first heart sound in a first cardiac cycle and a function of a first- or higher-order derivative of the portion of the first heart sound in a second cardiac cycle.

In Example 9, the morphology variation of the first heart sound of any one or more of Examples 1-8 optionally includes a timing of the first heart sound.

In Example 10, the atrial fibrillation detection circuit of any one or more of Examples 1-9 is optionally configured to provide an alert using the atrial fibrillation metric.

In Example 11, a method includes receiving heart sound information of a heart over a first interval, the first interval including at least a portion of each of a first number of cardiac cycles, determining an amplitude variation of a first heart sound of the heart sound information over the first interval using a heart sound variability circuit or determining a morphology variation of the first heart sound over the first interval using a heart sound variability circuit, and calculating, using an atrial fibrillation detection circuit, an atrial fibrillation metric indicative of an atrial fibrillation episode of the heart for the first interval using the determined amplitude variation or morphology variation.

In an example, the method can include determining the amplitude variation and the morphology variation, and calculating the atrial fibrillation metric using the determined amplitude and morphology variations.

In Example 12, any one or more of Examples 1-11 optionally includes determining, using the heart sound variability circuit, a variability score of the first heart sound for the first interval using the determined amplitude and morphology variations, wherein calculating the atrial fibrillation metric includes using the determined variability score.

In Example 13, any one or more of Examples 1-12 optionally includes receiving an electrical signal of the heart over the first interval using an electrical signal input circuit, receiving a heart sound signal of the heart using a heart sound signal input circuit, and detecting, using the heart sound signal input circuit, the first heart sound of the heart sound signal using the electrical signal of the heart.

In Example 14, determining the morphology variation of the first heart sound of any one or more of Examples 1-13 optionally includes determining a variation in a shape of the first heart sound.

In Example 15, determining the variation in the shape of the first heart sound of any one or more of Examples 1-14 optionally includes determining a variation in an offset between first and second features of the first heart sound in a first cardiac cycle an offset between the first and second features of the first heart sound in a second cardiac cycle.

In Example 16, determining the variation in the shape of the first heart sound of any one or more of Examples 1-15 optionally includes determining a variation in a function of a first- or higher-order derivative of a portion of the first heart sound in a first cardiac cycle and a function of a first- or higher-order derivative of the portion of the first heart sound in a second cardiac cycle.

In Example 17, determining the morphology variation of the first heart sound of any one or more of Examples 1-16 optionally includes determining a timing of the first heart sound.

In Example 18, any one or more of Examples 1-17 optionally includes providing an alert, using the atrial fibrillation detection circuit, based on the atrial fibrillation metric.

In Example 19, at least one machine readable medium includes instructions that, when executed by at least one processor, configure the at least one processor to receive heart sound information of a heart over a first interval, the first interval including at least a portion of each of a first number of cardiac cycles, determine an amplitude variation of a first heart sound of the heart sound information over the first interval using a heart sound variability circuit, determine a morphology variation of the first heart sound over the first interval using a heart sound variability circuit, and calculate, using an atrial fibrillation detection circuit, an atrial fibrillation metric indicative of an atrial fibrillation episode of the heart for the first interval using the determined amplitude and morphology variations.

In Example 20, the morphology variation of the first heart sound of any one or more of Examples 1-19 optionally includes at least one of a variation in a shape of the first heart sound, or a variation in a timing of the first heart sound, wherein the variation in the shape of the first heart sound includes at least one of an offset between first and second features of the first heart sound in a first cardiac cycle an offset between the first and second features of the first heart sound in a second cardiac cycle or a variation in a function of a first- or higher-order derivative of a portion of the first heart sound in a first cardiac cycle and a function of a first- or higher-order derivative of a portion of the first heart sound in a second cardiac cycle, wherein the at least one machine readable medium includes instructions that, when executed by the at least one processor, configure the at least one processor to provide an alert based on the atrial fibrillation metric.

In Example 21, a system or apparatus can include, or can optionally be combined with any portion or combination of any portions of any one or more of Examples 1-20 to include, means for performing any one or more of the functions of Examples 1-20, or a machine-readable medium including instructions that, when performed by a machine, cause the machine to perform any one or more of the functions of Examples 1-20.

The above detailed description includes references to the accompanying drawings, which form a part of the detailed description. The drawings show, by way of illustration, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system, comprising:
   an input circuit configured to receive heart sound information of a heart from a first interval, the first interval including at least a portion of each of a first number of cardiac cycles;
   a heart sound variability circuit configured to determine an amplitude variation of a first heart sound (S1) of the heart sound information, the amplitude variation representative of a variation of an amplitude of the S1 across the first number of cardiac cycles of the first interval; and
   an atrial fibrillation detection circuit configured to calculate an atrial fibrillation metric indicative of an atrial fibrillation episode of the heart for the first interval using the determined amplitude variation of the first interval.

2. The system of claim 1, wherein the amplitude variation includes a sum of a difference in magnitude of the first heart sound (S1) between individual cardiac cycles of the first number of cardiac cycles across the first interval.

3. The system of claim 1, wherein the amplitude variation includes a difference in magnitude of the first heart sound (S1) at a fiducial point for each cardiac cycle of the first number of cardiac cycles across the first interval.

4. The system of claim 1, wherein the heart sound variability circuit is configured to determine a morphology variation of the first heart sound (S1) across the first interval, and
   wherein the atrial fibrillation detection circuit is configured to calculate the atrial fibrillation metric indicative of the atrial fibrillation episode of the heart for the first interval using the determined amplitude and morphology variations.

5. The system of claim 4, wherein the heart sound variability circuit is configured to determine a variability score of the first heart sound (S1) for the first interval using the determined amplitude and morphology variations, and
   wherein the atrial fibrillation detection circuit is configured to calculate the atrial fibrillation metric using the variability score.

6. The system of claim 4, wherein the morphology variation of the first heart sound (S1) includes a variation in a shape of the first heart sound (S1).

7. The system of claim 6, wherein the variation in the shape of the first heart sound (S1) includes a variation in an offset between first and second features of the first heart sound (S1) in a first cardiac cycle and an offset between the first and second features of the first heart sound (S1) in a second cardiac cycle.

8. The system of claim 6, wherein the variation in the shape of the first heart sound includes a variation in a function of a first- or higher-order derivative of a portion of the first heart sound (S1) in a first cardiac cycle and a function of a first- or higher-order derivative of the portion of the first heart sound (S1) in a second cardiac cycle.

9. The system of claim 4, wherein the morphology variation of the first heart sound (51) includes a timing of the first heart sound (S1).

10. The system of claim 1, wherein the atrial fibrillation detection circuit is configured to provide an alert using the atrial fibrillation metric, and
    wherein the first interval is a short atrial fibrillation interval comprising a time of less than two minutes or a number of cardiac cycles occurring over a time of less than two minutes.

11. A method, comprising:
    receiving heart sound information of a heart from a first interval, the first interval including at least a portion of each of a first number of cardiac cycles;
    determining, using a heart sound variability circuit, an amplitude variation of a first heart sound (S1) of the heart sound information, the amplitude variation representative of a variation of an amplitude of the S1 across the first number of cardiac cycles of the first interval; and
    calculating, using an atrial fibrillation detection circuit, an atrial fibrillation metric indicative of an atrial fibrillation episode of the heart for the first interval using the determined amplitude variation of the first interval.

12. The method of claim 11, wherein the amplitude variation includes a difference in magnitude of the first heart sound (S1) at a fiducial point for each cardiac cycle of the first number of cardiac cycles across the first interval.

13. The method of claim 11, comprising:
    determining, using the heart sound variability circuit, a morphology variation of the first heart sound (S1) across the first interval,
    wherein calculating the atrial fibrillation metric includes using the determined amplitude and morphology variations.

14. The method of claim 13, comprising:
    determining, using the heart sound variability circuit, a variability score of the first heart sound (S1) for the first interval using the determined amplitude and morphology variations,
    wherein calculating the atrial fibrillation metric includes using the variability score.

15. The method of claim 13, wherein the morphology variation of the first heart sound (S1) includes a variation in a shape of the first heart sound (S1), or a timing of the first heart sound (S1).

16. At least one machine readable medium including instructions that, when executed by at least one processor, configure the at least one processor to:
    receive heart sound information of a heart from a first interval, the first interval including at least a portion of each of a first number of cardiac cycles;
    determine an amplitude variation of a first heart sound (S1) of the heart sound information, the amplitude variation representative of a variation of an amplitude of the S1 across the first number of cardiac cycles of the first interval; and
    calculate an atrial fibrillation metric indicative of an atrial fibrillation episode of the heart for the first interval using the determined amplitude variation of the first interval.

17. The at least one machine readable medium of claim 16, wherein the amplitude variation includes a difference in magnitude of the first heart sound (S1) at a fiducial point for each cardiac cycle of the first number of cardiac cycles across the first interval.

18. The at least one machine readable medium of claim 16, including instructions that, when executed by at least one processor, configure the at least one processor to:
- determine a morphology variation of the first heart sound (S1) across the first interval,
- wherein the instructions to calculate the atrial fibrillation metric include instructions that, when executed by at least one processor, configure the at least one processor to:
- calculate the atrial fibrillation metric using the determined amplitude and morphology variations.

19. The at least one machine readable medium of claim 18, including instructions that, when executed by at least one processor, configure the at least one processor to:
- determine a variability score of the first heart sound (S1) for the first interval using the determined amplitude and morphology variations,
- wherein the instructions to calculate the atrial fibrillation metric include instructions that, when executed by at least one processor, configure the at least one processor to:
- calculate the atrial fibrillation metric using the variability score.

20. The at least one machine readable medium of claim 18, wherein the morphology variation of the first heart sound (S1) includes a variation in a shape of the first heart sound (S1), or a timing of the first heart sound (S1).

* * * * *